(12) United States Patent
Allen et al.

(10) Patent No.: US 10,711,271 B2
(45) Date of Patent: Jul. 14, 2020

(54) METHOD FOR MAKING A CDNA LIBRARY

(71) Applicant: Bioo Scientific Corporation, Austin, TX (US)

(72) Inventors: Kevin Allen, Austin, TX (US); Adam Morris, Red Rock, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 277 days.

(21) Appl. No.: 15/818,469

(22) Filed: Nov. 20, 2017

(65) Prior Publication Data
US 2019/0153439 A1    May 23, 2019

(51) Int. Cl.
*C12N 15/10* (2006.01)

(52) U.S. Cl.
CPC .............. *C12N 15/1096* (2013.01)

(58) Field of Classification Search
CPC ................................ C12N 15/1096
USPC ........................................... 506/16
See application file for complete search history.

(56) References Cited

U.S. PATENT DOCUMENTS

2014/0128292 A1   5/2014  Toloue et al.
2018/0327853 A1*  11/2018  Adami ............... C12Q 1/6886

OTHER PUBLICATIONS

Cubas et al., "Integrative analysis of miRNA and mRNA expression profiles in pheochromocytoma and paraganglioma identifies genotype-specific markers and potentially regulated pathways", Endocrine-Related Cancer, 2013, 20: 477-493.
D'Alessio et al., "Second-strand cDNA synthesis with *E. coli* DNA polymerase I and RNase H: the fate of information at the mRNA 5' terminus and the effect of *E. coli* DNA ligase", Nucleic Acids Research, 1988, 16(5): 1999-2014.
Erster et al., "Use of RNase H and primer extension to analyze RNA splicing", Nucleic Acids Research, 1988, 16(13): 5999-6014.
Kraus et al., "Cloning and screening with nanogram amounts of immunopurified mRNAs: cDNA cloning and chromosomal mapping of cystathionine β-synthase and the β subunit of propionyl-CoA carboxylase", Proc. Natl. Acad. Sci., 1986, 83: 2047-2051.
Viollet et al., "Next-Generation Sequencing Analysis Reveals Differential Expression Profiles of MiRNA-mRNA Target Pairs in KSHV-Infected Cells", PLOS ONE, 2015, DOI:10.1371/journal.pone.0126439, 23 pages.
Thermofisher Scientific, "Reverse Transcription Reaction Setup—Seven Important Considerations", Aug. 12, 2016.

* cited by examiner

*Primary Examiner* — Karla A Dines
(74) *Attorney, Agent, or Firm* — James S. Keddie; Bozicevic, Field & Francis LLP

(57) ABSTRACT

This disclosure provides, among other things, a method for making a cDNA library. In some embodiments the method may comprise reverse transcribing mRNA to produce DNA:mRNA hybrids, treating the DNA:mRNA hybrids with RNAseH to produce mRNA fragments, and reverse transcribing the mRNA fragments.

19 Claims, 4 Drawing Sheets

METHOD FOR MAKING A CDNA LIBRARY

BACKGROUND

Total RNA samples typically contain RNA molecules that vary in length. For example, a total RNA sample obtained from mammalian cells may contain mRNA molecules (which generally range in size from a few hundred bases to several kb), lincRNA molecules (which are classified as being at least 200 bases in length), 18S and 28S rRNA molecules (which are approximately 1.9 kb and 5 kb, respectively), tRNA molecules (which are generally below 100 nt in length), and a variety of small RNA molecules (e.g., short interfering RNAs, microRNAs, tiny non-coding RNAs and small modulators RNAs) many of which are less than 30 nucleotides in length.

Conventional methods for sequencing the mRNAs and small RNAs in the same sample typically involve two workflows, one for the mRNA and the other for the small RNA. Such methods can be cumbersome.

SUMMARY

This disclosure provides, among other things, a method for making a cDNA library. In some embodiments the method may comprise reverse transcribing an RNA sample that comprises mRNA to produce a first strand cDNA product, treating the first strand cDNA product with RNAseH to produce mRNA fragments, and reverse transcribing the mRNA fragments. In some cases, the RNA sample may additionally comprise small RNAs (which are typically below 100 nucleotides in length and have a median length in the range of 18 to 40 nucleotides in length. In these embodiments, the method may comprise reverse transcribing the mRNA but not the small RNAs (e.g., using an oligo(dT) primer or one or more gene specific primers) to produce a product that contains the small RNAs and DNA:mRNA hybrids. RNAse treatment of this product produces a digestion product that can contain the small RNAs as well as fragments of the mRNA. In some embodiments the RNA fragments can be approximately the same length as the small RNAs and, in certain cases, can be copied into cDNA into the same reaction. As such, in some embodiments the method may comprise reverse transcribing the small RNAs and the mRNA fragments to produce a cDNA library, where the cDNA comprises cDNA copies of the small RNAs and cDNA copies of the mRNA fragments.

BRIEF DESCRIPTION OF THE FIGURES

Some aspects of the present invention may be best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
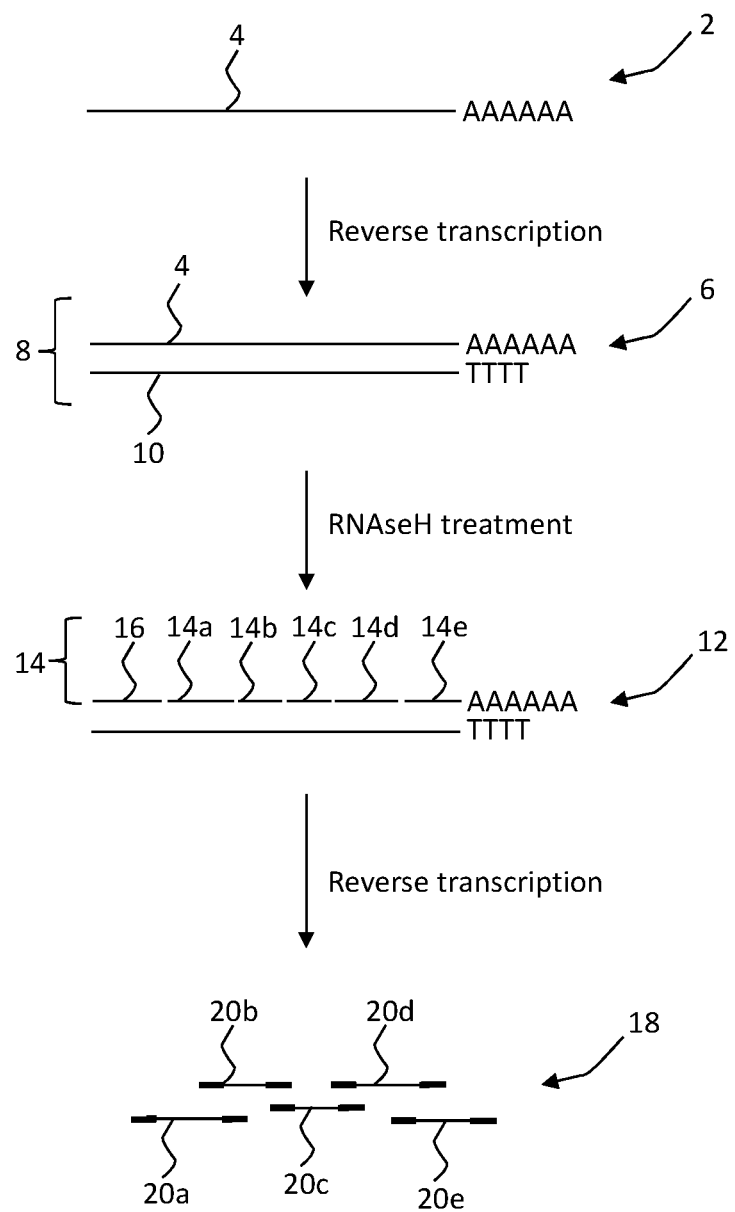
FIG. 1 schematically illustrates some of the principles of an embodiment of the present method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "RNA sample", as used herein, relates to a mixture of materials, typically, although not necessarily, in liquid form, containing one or more RNA molecules. An RNA sample may be obtained from cells, e.g., mammalian cells, for example. An RNA sample may contain a population of different RNA molecules, in which case it may contain more than 1,000, more than 10,000, more than 50,000, or more than 100,000 up to 1M or more different species of RNA, i.e., RNA molecules of different sequence. An RNA sample may contain mRNA molecules, which are typically at least 100 nt in length (e.g., 200 nt to 10 kb in length) and have a median length in the range of 500-5,000 nt. An RNA sample may additionally contain a variety of small non-coding regulatory RNAs that may be generically referred herein to as "small RNAs", e.g., short interfering RNAs, microRNAs, tiny non-coding RNAs, piwi-interacting small RNAs (piRNAs), snoRNAs and small modulatory RNAs. Small RNAs are typically below 100 nt in length and have a median length in the range of 18 nt to 40 nt. An RNA sample may additionally contain rRNA molecules, tRNA molecules, pre-miRNA molecules, snRNAs and long non-coding RNA molecules such as large intergenic RNA (lincRNA) molecules.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example. The term "duplex", "hybrid" or "double-stranded" as used herein refers to nucleic acids that have two strands that are bound together by based pairing.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be of 5-50 bases, e.g., 10 to 30 bases, in length or longer depending on the application. An adaptor may contain a molecular barcode, restriction sites and/or primer binding sites, depending on the application. In the methods described below, at least the 3' end of the adaptor can be RNA. In some embodiments, an adaptor can contain a molecular barcode (e.g., an "indexer" sequence).

As used herein, the terms "3'-OH" and "3'-hydroxyl" refer to a nucleotide at the 3' terminus of a nucleic acid, where the nucleotide has a hydroxyl group at the 3' position.

As used herein, the term "5'-P" or "5'-phosphate" refers to a nucleotide at the 5' terminus of a nucleic acid, where the nucleotide has a phosphate group at the 5' position.

As used herein, the term "cDNA library" refers to a collection of cDNAs synthesized from a template RNA. The cDNA library can be sequenced, labeled, amplified and/or cloned, depending on how it is going to be used.

As used herein, the term "RNA:cDNA hybrid" refers to a product after first-strand cDNA synthesis catalyzed by reverse transcriptase using RNA as a template. An "RNA-cDNA hybrid" can be full-length if the cDNA portion includes the complete sequence of the 5'-ends of the template mRNA.

As used herein, the term "template" refers to the substrate RNA for the reverse transcriptase to make cDNA. The template RNA is the target in a mixed population of RNA molecules for enrichment.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" or "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a composition, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "primer" refers an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Primers are usually single-stranded. Primers have a 3' hydroxyl.

The term "sequence-specific primer" is intended to refer to a primer that hybridizes to a unique sequence in mRNA or a target RNA. Sequence-specific primers do not have a random sequence and are not made of a single nucleotide. Random primers and oligo(dT) primers are not sequence specific primers.

The term "cDNA copy" refers to a DNA molecule that has the reverse complement of an RNA molecule (i.e., first strand cDNA) or a DNA molecule that has the same sequence as an RNA molecule except that the Us are T's (i.e., second strand cDNA).

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

FIG. 1 illustrates some of the principles of an embodiment of the method. With reference to FIG. 1, some embodiments of the method may comprise reverse transcribing RNA sample 2 that comprises mRNA 4 to produce first strand cDNA product 6. As shown, the first strand cDNA product 6 comprises DNA:mRNA hybrids 8 that comprise mRNA 4 and cDNA copy of the mRNA 10. In the embodiment shown in FIG. 1, the reverse transcription may be primed using an oligo(dT) primer (e.g., an anchored oligo(dT) primer). In other embodiments, the initial reverse transcription step may be done using one more. sequence-specific primers (e.g., primers that hybridize to unique sequences in the mRNA and/or short RNAs). The RNA sample may contain, for example, total cellular RNA, total RNA that has been depleted for one or more types of RNA (e.g., rRNA and/or tRNA), or mRNA and small RNA, for example, although other combinations are contemplated. In some embodiments, this step may be done by a "hot start" procedure in which two complementary mixtures are pre-heated to the incubation temperature prior to mixing them together. In these embodiments, the initial reverse transcription step may be done by: (i) pre-heating a first mixture comprising the primer and the RNA sample to a temperature in the range of 40-80 degrees, (ii) pre-heating a second mixture comprising the reverse transcriptase to a temperature in the range of 40-80 degrees, (iii) admixing the first and second mixtures to produce a reaction mix; and incubating the reaction mix at a temperature of 40-80 degrees for a sufficient time (e.g., at least 5 minutes), to produce the first strand cDNA product.

As shown in FIG. 1, the method may comprise treating the first stand cDNA product 6 with RNAseH to produce a digested sample 12 that comprises fragments of the mRNA 14 (e.g., fragments 14a, 14b, 14c, 14d and 14e). In practice, the number fragments of mRNA per DNA:mRNA hybrid may vary greatly based on the length of the DNA:mRNA hybrids and the number of cleavage events that occur per DNA:mRNA hybrid (i.e., the number of times the RNAseH nicks the mRNA molecule of the DNA:mRNA hybrid). In some embodiments, at least 90% of the DNA:mRNA hybrids may give rise to approximately 4 to 200 DNA:mRNA hybrids each. The median length of fragments 14 may be at least 20 nucleotides (e.g., in the range of 20 to 100 or 20 to 50 nucleotides). As will be described in greater detail below, except for fragment 16 at the 5' end of the mRNA, all of the fragments should have a 5' phosphate and a 3' hydroxyl and, as such, can be processed in the same way. The 5' end fragment 16 can be treated enzymatically to contain a 5' phosphate, if necessary.

Several reverse transcriptases (e.g., the wild type MMLV and HIV reverse transcriptases) have an intrinsic RNAseH activity and, as such, in some embodiments of the method the reverse transcriptase and RNAseH activities required for the initial steps of the method may be provided by a single enzyme. In these embodiments, an RNAseH$^+$ reverse transcriptase can be used. In other embodiments, the reverse transcriptase and RNAseH activities required for the initial steps of the method are provided by different enzymes. In these embodiments, the reverse transcription step may be done using an RNAaseH$^-$ reverse transcriptase, and the RNAseH treatment may be done using a separate enzyme. In some embodiments, the reverse transcription and/or the RNAseH may thermostable. In some embodiments, the initial reverse transcription step may be done at temperature in the range of 40° C. to 80° C. In some embodiments, the RNAseH treatment step may be done at a temperature in the range of 40° C. to 80° C., e.g., at a temperature in the range of 60° C. to 80° C. It is thought that at an elevated temperature incompletely digested mRNA fragments (e.g., fragments that have a median length in the range of 15 to 50 nucleotides) produced by RNAseH cleavage start to become disassociated from the cDNA to which they were bound. RNAseH requires a double-stranded substrate, and because their disassociation prevents the fragments from being a substrate for the RNAseH, mRNA fragments in the range of 15 to 50 nucleotides should not be digested any further, even in an extended incubation. Thus, in some embodiments, the reaction conditions (the salt concentration and temperature) can be adjusted to produce fragments of a pre-determined length. Higher salt and/or a higher incubation temperature should, in theory, result in a population of fragments that have a longer median length and lower salt and/or a lower incubation temperature should, in theory, result in a population of fragments that have a shorter median length. The length of the fragments 14 can also be tailored by modifying the amount of enzyme used and/or the incubation conditions and/or by altering total RNA input concentration. In some embodiments, in order to avoid complete digestion of the mRNAs and to obtain mRNA fragments of the desired length, the amount of RNAseH used in the RNAseH treatment may be less than a tenth of the amount of RNAseH used for other reactions. For example, if 5 units of RNAseH are typically used to digest mRNA to completion, then 0.1 to 0.5 units of RNAseH (e.g., an amount in the range of 0.3 to 0.16 units) may be used in the present method, where one unit of RNaseH is the amount of enzyme which produces 1 nmol acid soluble ribonucleotides from [3H]poly(A)×poly (dT) in 20 minutes at 37° C. under the conditions used, using the method of Hillenbrand and Saudenbauer (Nucleic Acids Res. 1982 10:833).

Figure 2:
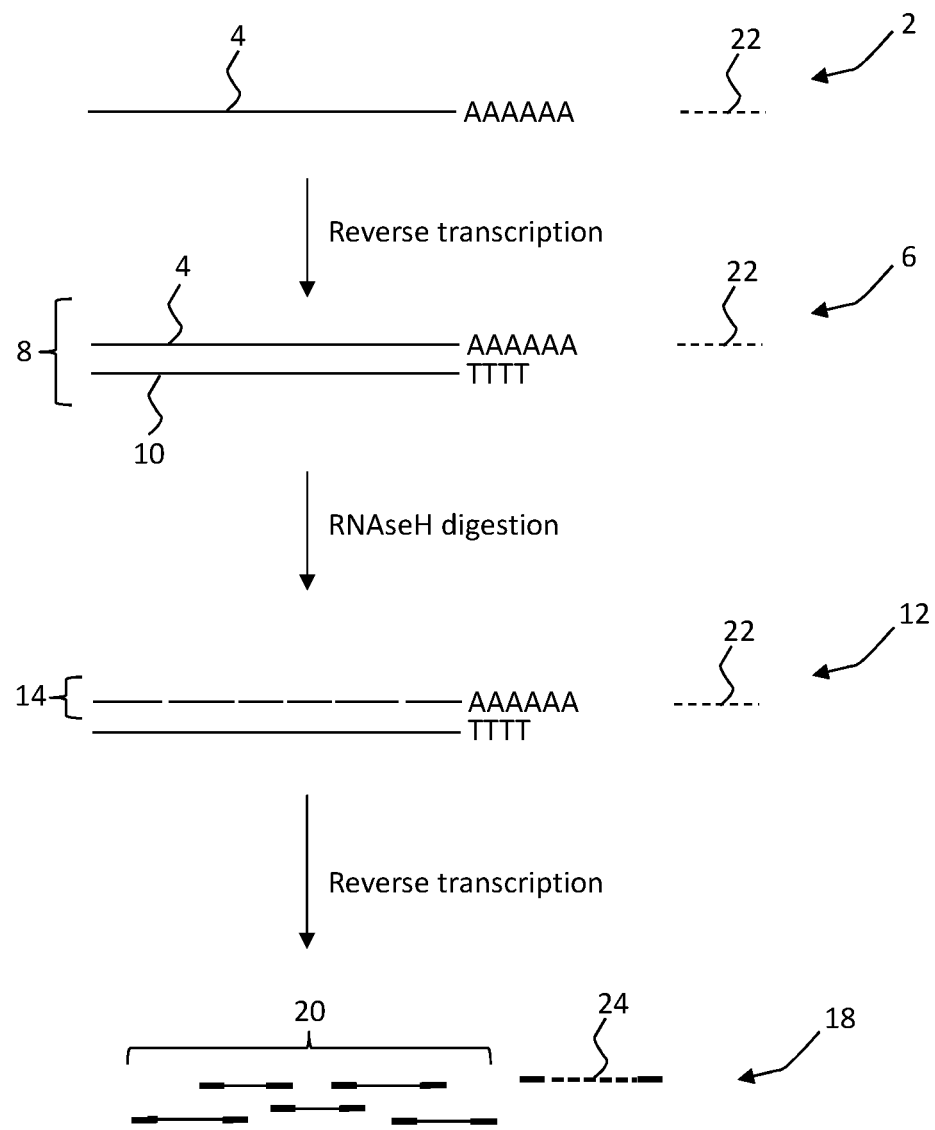
FIG. 2 schematically illustrates some of the principles of another embodiment of the present method.

Next, the method may comprise reverse transcribing the mRNA fragments to produce a cDNA library 18. The fragments may be reverse transcribed using any suitable method and, in some embodiments, the fragments may be reverse transcribed by ligating a 5' adaptor to the fragments, tailing the 3' end of the fragments using polyA polymerase, and reverse transcribing the fragments using an oligo(dT) primer. As would be apparent, the ligating and tailing steps can be done in any order. For example, in some embodiments, the 5' adaptors may be ligated prior to tailing and in other embodiments the tailing may be done prior to tailing. In some embodiments the adaptor may be a single-stranded oligonucleotide in the range of 5 to 20 nt in length (e.g., 6, 7, 8, 9, 10, 11 or 12 nt in length), although adaptors having a length outside of this range may also be employed. The adaptor may be an RNA oligonucleotide, a DNA oligonucleotide or an oligonucleotide that comprises DNA and RNA. The adaptor may be ligated onto the RNA molecules of the digested sample using an RNA ligase, e.g., T4 RNA ligase, using any of the methods outlined in Wang et al (RNA 2007 13: 151-159) or Lockhart et al (U.S. Pat. No. 6,344,316) among many others. This part of the method will be described in greater detail below. In the example shown in FIG. 1, the cDNA library 18 may comprise cDNA molecules 20a, 20b, 20c, 20d and 20e, which cDNA molecules correspond to RNA fragments 14a, 14b, 14c, 14d and 14e, respectively. As would be apparent, the number of cDNA molecules in the cDNA library can vary greatly depending on the complexity of the mRNAs in RNA sample 2, their length, and how the mRNAs are fragmented. The cDNA library may be optionally amplified and sequenced, methods for which will be described in greater detail below. In these methods, the cDNA that is made in the first step of the method (i.e., the copy of the mRNA 10) is not itself analyzed and, as such, the cDNA molecules made in the initial step of the may be degraded (e.g., using a DNAse treatment), discarded (e.g., purified away from the cDNA in the library by size separation) and/or diluted out (by preferentially amplifying the cDNA molecules in the cDNA library) prior to sequencing. In some embodiments, the method may be used to make a cDNA library that represents the mRNA and small RNA fractions in an RNA sample. In these embodiments, the small RNAs are not transcribed in the first reverse transcription step in the method. These embodiments of the method are described in FIG. 2. With reference to FIG. 2, in some embodiments RNA sample 2 contains small RNAs 22 that are less than 50 nucleotides in length and have a median length in the range of 18 nt to 40 nt, in addition to mRNA 4. In these embodiments, the first reverse transcription step of the method may comprise reverse transcribing the mRNA 4 but not the small RNAs 22 in RNA sample 2. Preferential reverse transcription of the mRNA may be done using an oligo(dT) primer (as shown in FIG. 2) or one or more gene specific primers, for example. RNAseH requires an DNA: mRNA hybrid and, as such, only the mRNAs that have been reverse transcribed (and not the small RNAs or other types of RNA that have not been reverse transcribed) should be cleaved by the RNAseH. In these embodiments: (i) the first strand cDNA product 6 contains the small RNAs 22 and the DNA:mRNA hybrids 8, and (ii) the digested sample 12 contains the small RNAs 22 and the mRNA fragments 14. If small RNAs are present in the sample, then the mRNAs are generally fragmented to a median length that is similar to the length of the small RNAs. Small RNAs can be in the range of 18-29 nucleotides in length, and many small RNAs are approximately 19-25 nucleotides in length. As such, the mRNAs may be fragmented to a median length of between 15 to 100 nucleotides, e.g., 15 to 50 nucleotides. In these embodiments, the next step involves reverse transcribing the small RNAs 22 and the mRNA fragments 14 to produce the cDNA library 18. As shown, the cDNA library comprises: i. copies of the small RNAs 24 and ii. copies of the mRNA fragments 20. In these embodiments, both the small RNAs and the mRNA fragments have a 5' phosphate and a 3' hydroxyl and, as such, can be reverse transcribed in the same reaction (e.g., by ligating a 5' adaptor to any RNA molecules that have a 5' phosphate, tailing the 3' end of any RNA molecules that contain a 3' hydroxyl using polyA polymerase, and reverse transcribing any molecules that have been tailed using an oligo(dT) primer, for example). The cDNA library may contain the first strand cDNA made in the initial step of the method, or not. In some cases, the first strand cDNA made in the initial step of the method may have been removed or degraded prior to making the cDNA library. The cDNA library may also contain cDNA copies of molecules that have not been ligated to a 5' end adaptor. However, as will be described in greater detail below, these molecules should not be amplified and, as such, are not represented in the amplification product.

Figure 3:
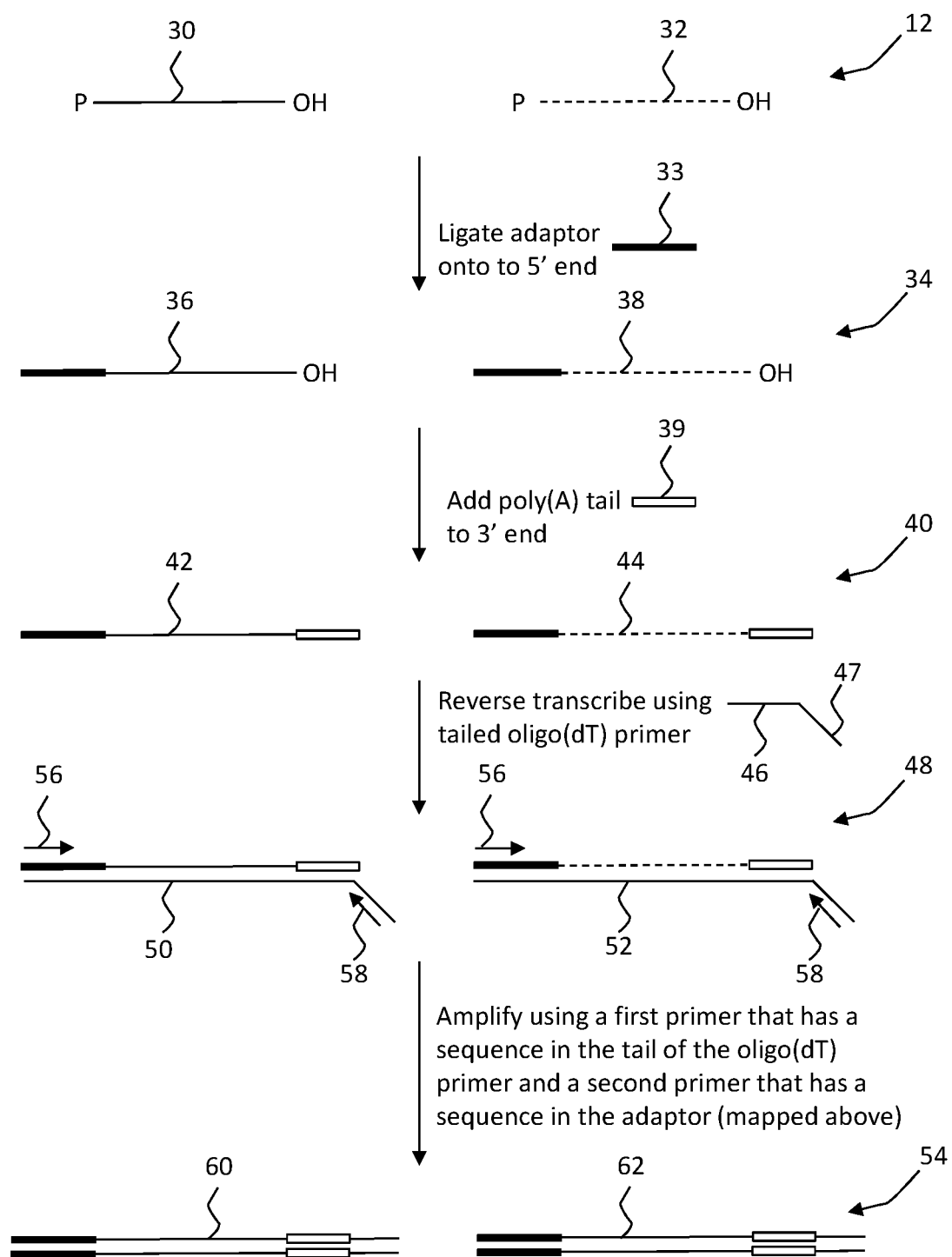
FIG. 3 schematically illustrates an example of how a cDNA library can be made.

One way that the second reverse transcription reaction can be performed is illustrated in FIG. 3. The method illustrated in FIG. 3 is illustrative only and is not the only way to make cDNA from the fragments. In the method illustrated in FIG. 3, the digested sample 12 contains mRNA fragments 30 as well as small RNAs 32, as described above. However, the method can be performed on samples that do not contain small RNAs in some cases. In this method, the second reverse transcription may be done by ligating an adaptor 33 to the 5' end of the RNA molecules in the digested sample (i.e., the 5' end of the RNA molecules that contain a 5' phosphate group in the digested sample) to produce adaptor-ligated RNAs 34. Because the RNA fragments and the small RNAs both contain a 5' phosphate group, this ligation step should produce adaptor-ligated RNA fragments 36 as well as adaptor-ligated small RNAs 38. The RNA ligase used in the method can be any suitable ligase. In some embodiments, T4 RNA ligase can be used, although a variety of other RNA ligases that have a preference for single-stranded substrates can be used instead. In some embodiments, the RNA ligase used may be thermostable. In these embodiments, the ligation reaction may be done at an elevated temperature that may be in the range of 40 to 80° C. Next, the method may comprise adding a poly(A) tail 39 to the 3' end of the adaptor-ligated RNAs 34 to produce A-tailed, adaptor ligated RNAs 40. This step may be done by incubating the adaptor-ligated RNAs 34 with a poly(A) polymerase and, because the RNA fragments and the small RNAs both contain a 3' hydroxyl group, the poly(A) tailing step should produce adaptor-ligated, tailed, RNA fragments 42 as well as adaptor-ligated, tailed, small RNAs 44.

The method described above is not the only way to convert the RNA fragment into cDNA. For example, in alternative embodiments, another adaptor (a "3' adaptor") can be added to the 3' end of the RNA molecules by ligation. Also, the 3' end of the RNA fragments can be processed before the 5' end of the RNA fragments. As such, in some embodiments, the method may comprise adding an A-tail or an adaptor (a "3' adaptor") to the 3' end of the RNA molecules in the digested sample (i.e., by incubating the sample with a poly(A) polymerase and rATP or by incubating the sample with a ligase and the 3' adaptor), ligating an adaptor to the 5' end of the RNA molecules in the digested sample; and reverse transcribing the A-tailed, adaptor ligated RNAs using a primer that hybridizes to the A-tail or the adaptor added to the 3' of the RNA molecules, to produce the cDNA library, wherein the adding and ligating steps may be done in either order.

The cDNA library 48 may be produced by reverse transcribing the A-tailed, adaptor ligated RNAs 40 using an oligo-dT primer 46. Because the adaptor-ligated, tailed, RNA fragments 42 contain a 5' adaptor and a 3' poly(A) tail to which the oligo-dT primer 46 should prime cDNA synthesis, the cDNA library 48 should contain cDNA copies of the adaptor-ligated, tailed, mRNA fragments 50 as well as cDNA copies of the adaptor-ligated, tailed, small RNAs 52. In the embodiment shown, oligo(dT) primer 46 contains an optional 5' tail 47, which does not hybridize to the A-tailed, adaptor ligated RNAs 40. As shown in FIG. 3, the cDNA library 48 may be optionally amplified by PCR to produce an amplification product 54. This step may be done using a first primer 56 that has a 3' end that is the same as a sequence in the adaptor and a second primer 58 that has a 3' end that is the same as a sequence in the sequence in the tail of the oligo(dT) primer. As shown, the amplification product 54 contains amplicons of the mRNA fragments 60 as well as amplicons of the small RNAs 62, both of which can be analyzed, e.g., sequenced, in the same workflow. In some embodiments, the amplification product may be subjected to a size selection step to remove unincorporated primers and/or unwanted species such as rRNA fragments or snoRNAs prior to analysis.

In embodiments in which the cDNAs are sequenced, the cDNA library may be amplified using one or more primers that hybridize to the added sequences (or their complements), as described above. In some embodiments, the primers used may have sequences that are compatible with the sequencing platform being used (e.g., P5 and P7 sequences, which sequences are compatible with Illumina's sequencing platform) and the amplification products will have those sequences at their ends (e.g., P5 sequence at one and the P7 sequence at the other, if the Illumina sequencing platform is being used).

The sequencing step may be done using any convenient next generation sequencing method and may result in at least 10,000, at least 50,000, at least 100,000, at least 500,000, at least 1M, at least 10M, at least 100M or at least 1 B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

In certain embodiments, the cDNA that is sequenced may comprise a pool of cDNAs libraries made from a plurality of different RNA samples, wherein the different cDNA libraries have a molecular barcode (in the adaptor or PCR primers) to indicate their source. In some embodiments the cDNAs being analyzed may be derived from a single source (e.g., a single organism, virus, tissue, cell, subject, etc.), whereas in other embodiments, the cDNAs that are sequenced may be a pool of nucleic acids extracted from a plurality of sources (e.g., a pool of nucleic acids from a plurality of organisms, tissues, cells, subjects, etc.), where by "plurality" is meant two or more. As such, in certain embodiments, a cDNAs that are sequenced can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. The sequence reads may be analyzed by a computer and, as such, instructions for performing the steps set forth below may be set forth as programing that may be recorded in a suitable physical computer readable storage medium.

The method described herein can be employed to analyze mRNA and small RNAs from virtually any organism and/or sample-type, including, but not limited to, plants, animals (e.g., reptiles, mammals, insects, worms, fish, etc.), tissue samples, cadaveric tissue, archaeological/ancient samples, etc. In certain embodiments, the RNA sample used in the method may be derived from a mammal, where in certain embodiments the mammal is a human. In exemplary embodiments, the RNA sample may contain RNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the RNA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cfRNA obtained from blood, e.g., from the blood of a pregnant female or a patient.

The present method may be employed in a variety of diagnostic, drug discovery, and research applications that include, but are not limited to, diagnosis or monitoring of a disease or condition (where the expression of an mRNA and/or small RNA provides a marker for the disease or condition), discovery of drug targets (where an mRNA and/or small RNA is differentially expressed in a disease or condition and may be targeted for drug therapy), drug screening (where the effects of a drug are monitored by assessing the level of an mRNA and/or small RNA), determining drug susceptibility (where drug susceptibility is associated with a particular profile of an mRNA and/or small RNA) and basic research (where is it desirable to identify the presence of an mRNA and/or small RNA in a sample, or, in certain embodiments, the relative levels of a particular mRNA and/or small RNA in two or more samples).

In certain embodiments, relative levels of an mRNA and/or small RNA in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the mRNA and/or small RNA profiles of two or more different samples may be compared to identify mRNAs and/or small RNAs that are associated with a particular disease or condition (e.g., an mRNA and/or small RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., a normal cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

In some embodiments, the sequence reads may be analyzed to provide a quantitative determination of which sequences are in the sample. This may be done by, e.g., counting sequence reads or, alternatively, counting the number of original starting molecules, prior to amplification, based on their fragmentation breakpoint and/or whether they contain the same indexer sequence (which can be present in the 5' adaptor, for example). The use of molecular barcodes in conjunction with other features of the fragments (e.g., the end sequences of the fragments, which define the breakpoints) to distinguish between the fragments is known. Molecular barcodes and exemplary methods for counting individual molecules are described in Casbon (Nucl. Acids Res. 2011, 22 e81) and Fu et al (Proc Natl Acad Sci USA. 2011 108: 9026-31), among others. Molecular barcodes are described in U.S. 2015/0044687, U.S. 2015/0024950, U.S. 2014/0227705, U.S. Pat. No. 8,835,358 and U.S. Pat. No. 7,537,897, as well as a variety of other publications.

Also provided is a method for identifying a pattern that correlates with phenotype, e.g., a disease, condition or clinical outcome, etc. In some embodiments, this method may comprise (a) performing the above-described method on a plurality of RNA samples, wherein the RNA samples are isolated from patients having a known phenotype, e.g., disease, condition or clinical outcome, thereby determining which RNAs from each of the patients; and (b) identifying a signature that is correlated with the phenotype.

In some embodiments, the signature may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

Also provided is a method for analyzing a patient sample. In this embodiment, the method may comprise: (a) identifying, using the above-described method, sequences that are under and/or over expressed in a patient; (b) comparing the identified sequences to a set of signature sequences that are correlated with a phenotype, e.g., a disease, condition, or clinical outcome etc.; and (c) providing a report indication a correlation with phenotype. This embodiment may further comprise making a diagnosis, prognosis or theranosis based on the results of the comparison.

In some embodiments, the method may involve creating a report as described above (an electronic form of which may have been forwarded from a remote location) and forwarding the report to a doctor or other medical professional to determine whether a patient has a phenotype (e.g., cancer, etc) or to identify a suitable therapy for the patient. The report may be used as a diagnostic to determine whether the subject has a disease or condition, e.g., a cancer. In certain embodiments, the method may be used to determine the stage or type cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the report may be analyzed by an MD or other qualified medical professional, and a report based on the results of the analysis of the image may be forwarded to the patient from which the sample was obtained.

Accordingly, among other things, the instant methods may be used to link the expression of certain genes to certain physiological events.

Embodiments

Embodiment 1. A method for making a cDNA library, comprising:
(a) reverse transcribing an RNA sample that comprises mRNA to produce a first strand cDNA product;
(b) treating the first stand cDNA product with RNAseH to produce a digested sample that comprises fragments of the mRNA; and
(c) reverse transcribing the mRNA fragments to produce a cDNA library.

Embodiment 2. The method of embodiment 1, further comprising sequencing the cDNA library to obtain sequence reads corresponding to at least some of the mRNA fragments.

Embodiment 3. The method of embodiment 1, wherein:
the RNA sample of step (a) further comprises small RNAs, step (a) comprises reverse transcribing the mRNA but not the small RNAs to produce a first strand cDNA product that contains the small RNAs and DNA:mRNA hybrids;
the digested sample of step (b) contains the small RNAs and the mRNA fragments; and
step (c) comprises reverse transcribing the small RNAs and the mRNA fragments to produce the cDNA library, wherein the cDNA library comprises: i. copies of the small RNAs and ii. copies of the mRNA fragments.

Embodiment 4. The method of embodiment 3, wherein the small RNAs include short interfering RNA (siRNA) molecules, microRNA (miRNA) molecules, tiny non-coding RNA (tncRNA) molecules or small modulatory RNA (smRNA) molecules.

Embodiment 5. The method of embodiment 3, further comprising sequencing the cDNA library to obtain sequence reads corresponding to at least some of the mRNA fragments and sequence reads corresponding to at least some of the small RNAs.

Embodiment 6. The method of any prior embodiment, wherein step (c) is done by:
(i) adding a tail or an adaptor to the 3' end of the RNA molecules in the digested sample;
(ii) ligating an adaptor to the 5' end of the RNA molecules in the digested sample; and
(iii) reverse transcribing the tailed, adaptor ligated RNAs using a primer that hybridizes to the tail or adaptor added to the 3' of the RNA molecules, to produce the cDNA library, wherein the adding step (i) and the ligating step (ii) can be done in either order.

Embodiment 7. The method of any prior embodiment, wherein the reverse transcription of step (a) is primed by an oligo-dT primer.

Embodiment 8. The method of any of embodiments 1-6, wherein the reverse transcription of step (a) is primed by a sequence-specific primer.

Embodiment 9. The method of any prior embodiment, wherein the method comprises amplifying the cDNA library by PCR.

Embodiment 10. The method of embodiment 9, further comprising a post-PCR size selection.

Embodiment 11. The method of any prior embodiment, wherein step (a) is done using an RNAaseH⁻ reverse transcriptase.

Embodiment 12. The method of any prior embodiment, wherein the reverse transcriptase activity of step (a) and the RNAaseH activity of step (b) are provided by a single enzyme.

Embodiment 13. The method of any of embodiments 1-11, wherein the reverse transcriptase activity of step (a) and the RNAaseH activity of step (b) are provided by different enzymes.

Embodiment 14. The method of any prior embodiment, wherein the RNAase H is thermostable.

Embodiment 15. The method of embodiment 14, wherein the RNAase H treatment of of step (b) is done at temperature in the range of 40° C. to 80° C.

Embodiment 16. The method of any prior embodiment, wherein the fragments produced in step (b) have a median size of below 50 nucleotides.

Embodiment 17. The method of any prior embodiment, wherein the RNAseH digestion of step (b) is done using 0.1 units to 0.5 units of RNAseH.

Embodiment 18. The method of any prior embodiment, wherein step (a) is done by:

pre-heating a first mixture comprising the primer and the RNA sample to a temperature in the range of 40-80 degrees;

pre-heating a second mixture comprising a thermostable reverse transcriptase to a temperature in the range of 40-80 degrees; and admixing the first and second mixtures to produce a reaction mix; and incubating the reaction mix at a temperature of 40-80 degrees for at least 5 minutes, to produce the first strand cDNA product.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

Step A: Reverse Transcription and Rnase H Digestion of mRNA

1. For each sample, combine the following reagents on ice in a nuclease-free 96-well plate and mix well:

| | |
|---|---|
| 10 uL | total RNA (5 ng total) |
| 4 uL | Nuclease-free Water |
| 1 uL | Anchored Oligo(dT) Primer |
| 15 uL | TOTAL |

2. In a clean microcentrifuge tube, prepare a master mix using the following volumes per reaction. Make enough master mix to give a 10% overage. Prepare on ice then allow master mix to equilibrate to room temperature.

| | |
|---|---|
| 4 uL | RT/Rnase H Buffer |
| 1 uL | NEXTflex RT enzyme |
| 5 uL | Master Mix per reaction |

3. Program a thermocycler as follows:

| | | |
|---|---|---|
| 2 min | 70° C. | |
| pause | 50° C. | ← Step 5: add 5 uL Master Mix then proceed |
| 30 min | 50° C. | |
| pause | 70° C. | ← Step 7: add 2 uL Rnase H Enzyme Mix then proceed |
| 15 min | 70° C. | |
| hold | 4° C. | |

4. Place the tubes containing RNA and anchored oligo (dT) primer in the thermocycler and start the program.

5. Once the thermocycler has finished ramping down from 70° C. to 50° C., add 5 uL room temperature Master Mix to each 15 uL reaction and mix thoroughly by pipetting.

6. While the thermocycler is holding at 50° C. for 30 min, prepare the Rnase H Enzyme Mix. Prepare enough to give a 10% overage.

| | |
|---|---|
| 1.5 uL | Rnase H Dilution Buffer |
| 0.5 uL | Rnase H Enzyme |
| 2 uL | Rnase H Enzyme Mix |

7. Once the thermocycler has finished ramping up from 50° C. to 70°, add 2 uL Rnase H Enzyme Mix to each sample and mix thoroughly by pipetting.

8. After thermocycling has finished, proceed immediately to Step B: Bead Cleanup.

Step B: Bead Cleanup

1. To each sample, add 20 uL of NEXTflex Cleanup Beads and mix well by pipette.

2. Add 100 uL 100% ethanol and mix well by pipette.

3. Incubate for 5 minutes.

4. Magnetize sample for 5 minutes or until solution is clear.

5. Remove and discard supernatant.

6. Add 180 µL of freshly prepared 80% ethanol, incubate for 30 seconds, and remove all of the supernatant. Repeat this step for a total of 2 ethanol washes. IMPORTANT: Always use freshly prepared 80% ethanol and do not incubate the bead pellet with 80% ethanol for extended periods.

7. Incubate sample for 3 minutes. After one minute, remove all residual liquid that may have collected at the bottom of the well.

8. Remove plate from magnetic stand and resuspend bead pellet in 13 uL Nuclease-free Water by pipetting volume up and down. Ensure that beads are completely resuspended.

9. Incubate sample for 2 minutes.

10. Magnetize sample for 3 minutes or until solution appears clear.

11. Transfer 11 uL of supernatant to a new well.

Step C: Polyadenylation

1. For each sample, combine the following reagents on ice in a nuclease-free 96-well plate and mix well:

| | |
|---|---|
| 11 uL | RNA (from Step B) |
| 1.5 uL | ATP |
| 12.5 uL | TOTAL |

2. In a separate Eppendorf tube, on ice, prepare enough of the following master mix for all samples. Combine and mix immediately. Per reaction:

| | |
|---|---|
| 1.5 uL | NEXTflex Polyadenylation Buffer |
| 1 uL | Poly-A Polymerase Enzyme |
| 2.5 uL | Master Mix per reaction |

3. Add 2.5 uL of master mix to each sample and mix thoroughly by pipetting.

4. Incubate as follows:

| | |
|---|---|
| 15 min | 37° C. |
| 20 min | 65° C. |
| hold | 4° C. |

5. Proceed to Step D: NEXTflex 5' 4N Adapter Ligation.

Step D: NEXTflex 5' 4N Adapter Ligation

1. For each sample, combine the following reagents on ice in a nuclease-free 96-well plate:

| | |
|---|---|
| 15 uL | Polyadenylated RNA (from Step C) |
| 7.5 uL | 5' Ligation Buffer Mix |
| 1.5 uL | NEXTflex 5' 4N Adapter |
| 2 uL | 5' Ligation Enzyme Mix |
| 26 uL | TOTAL |

2. Mix thoroughly by pipetting.

3. Incubate at 20° C. for 1 hour in a thermocycler with heated lid turned off or left open.

4. Proceed to Step E: Reverse Transcription-First Strand Synthesis.

Step E: Reverse Transcription-First Strand Synthesis

1. In a separate Eppendorf tube, prepare a master mix using the following volumes per reaction. Make enough master mix to give a 10% overage. Prepare on ice then allow master mix to equilibrate to room temperature.

| | |
|---|---|
| 12 uL | NEXTflex RT Buffer Mix |
| 2 uL | NEXTflex RT enzyme |
| 14 uL | Master Mix per reaction |

2. Program a thermocycler as follows:

| | | |
|---|---|---|
| 2 min | 70° C. | |
| pause | 50° C. | ← Step 4: add 14 uL Master Mix then proceed |
| 32 min | 50° C. | |
| 5 min | 90° C. | |
| hold | 4° C. | |

3. Place the polyadenylated and 5'-ligated RNA from Step D in the thermocycler and start the program.

4. Once the thermocycler has finished ramping down from 70° C. to 50° C., add 14 uL room temperature Master Mix to each 26 uL reaction and mix thoroughly by pipetting.

5. After thermocycling has finished, proceed to Step F.

Step F: Bead Cleanup

1. To each sample, add 40 uL of Adapter Depletion Solution and mix well by pipette.

2. Add 40 uL of NEXTflex Cleanup Beads and mix well by pipette.

3. Add 90 uL isopropanol and mix well by pipette.

4. Incubate for 5 minutes.

5. Magnetize sample for 5 minutes or until solution is clear.

6. Remove and discard supernatant.

7. Add 180 μL of freshly prepared 80% ethanol, incubate for 30 seconds, and remove all of the supernatant. Repeat this step for a total of 2 ethanol washes. IMPORTANT: Always use freshly prepared 80% ethanol and do not incubate the bead pellet with 80% ethanol for extended periods.

8. Incubate sample for 3 minutes. After one minute, remove all residual liquid that may have collected at the bottom of the well.

9. Remove plate from magnetic stand and resuspend bead pellet in 20 uL Nuclease-free Water by pipetting volume up and down. Ensure that beads are completely resuspended.

10. Incubate sample for 2 minutes.

11. Magnetize sample for 3 minutes or until solution appears clear.

12. Transfer 18 uL of supernatant to a new well.

13. Proceed to Step G: PCR Amplification.

Step G: PCR Amplification

1. For each sample, combine the following reagents on ice in a nuclease-free 96-well PCR plate:

| | |
|---|---|
| 18 uL | Purified First Strand Synthesis Product (from Step F) |
| 1 uL | NEXTflex Universal Primer |
| 1 uL | NEXTflex Barcode Primer (a different barcoded primer should be used for each sample that will be multiplexed for sequencing) |
| 5 uL | NEXTflex PCR Master Mix |
| 25 uL | TOTAL |

2. Cycle as follows (make sure thermocycler is above 80° C. before placing samples on block):

| | | |
|---|---|---|
| 2 min | 95° C. | |
| 20 sec | 95° C. | |
| 30 sec | 65° C. | ← Repeat 10-35 cycles |
| 15 sec | 72° C. | |
| 2 min | 72° C. | |

3. Proceed to Step H: Size Selection & Cleanup.

Step H: Size Selection & Cleanup

1. Ensure the volume of all samples is 25 uL. If less, add Nuclease-free Water to bring the entire volume up to 25 uL.
2. To each sample, add 45 uL of NEXTflex Cleanup Beads and mix well by pipette.
3. Incubate for 5 minutes.
4. Magnetize sample for 5 minutes or until solution is clear.
5. Remove and discard supernatant.
6. Add 180 µL of freshly prepared 80% ethanol, incubate for 30 seconds, and remove all of the supernatant. Repeat this step for a total of 2 ethanol washes. IMPORTANT: Always use freshly prepared 80% ethanol and do not incubate the bead pellet with 80% ethanol for extended periods.
7. Incubate sample for 3 minutes. After one minute, remove all residual liquid that may have collected at the bottom of the well.
8. Remove plate from magnetic stand and resuspend bead pellet in 13.5 uL Nuclease-free Water by pipetting volume up and down. Ensure that beads are completely resuspended.
9. Incubate sample for 2 minutes.
10. Magnetize sample for 3 minutes or until solution appears clear.
11. Transfer 12 uL of supernatant to a new well or clean microcentrifuge tube. This is the sequencing library.
12. If necessary, check the size distribution of the final library.

Example 2

Figure 4:
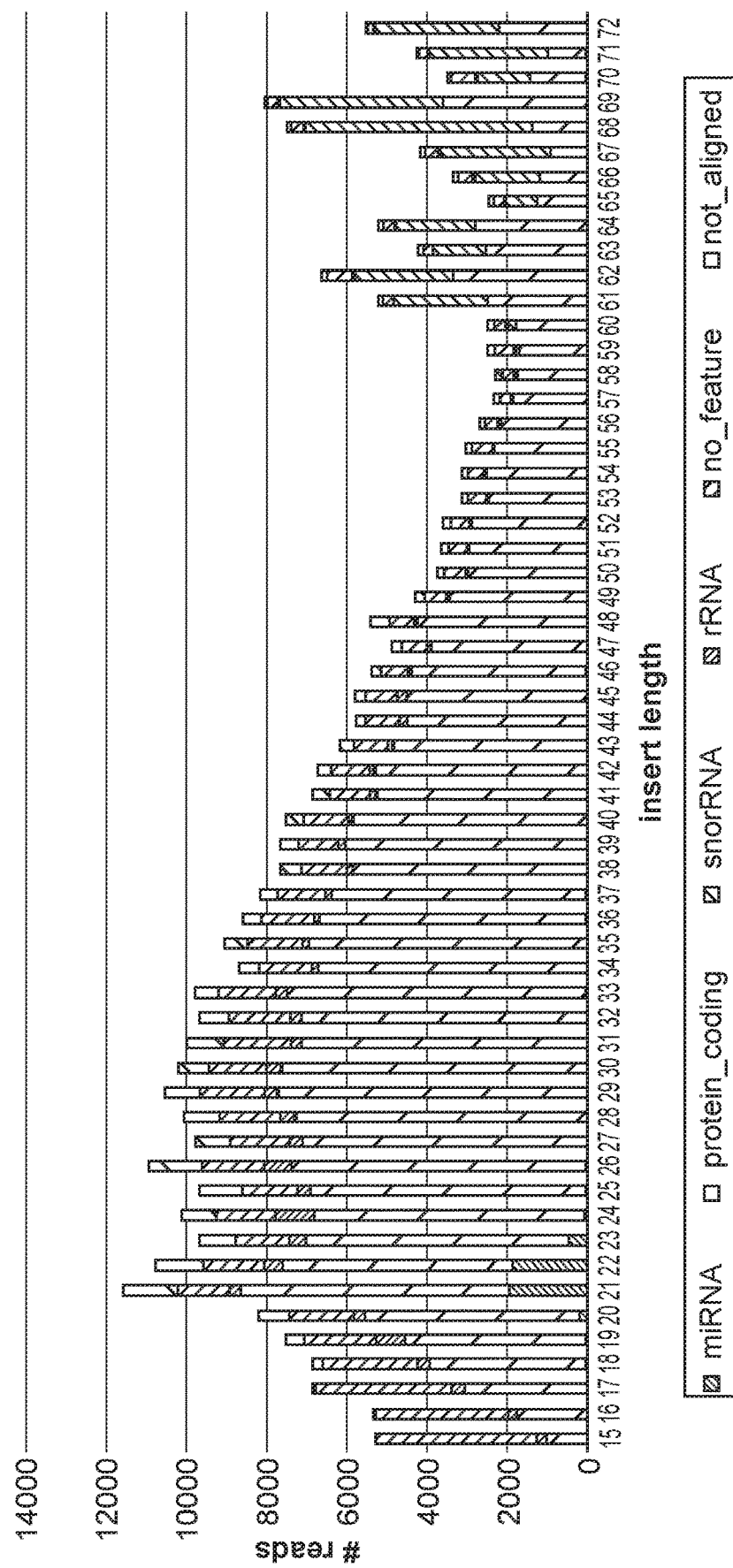
FIG. 4 is a graph showing the number of reads at each insert length.

Libraries were made using 10 ng of total RNA from MCF7 cells according to the protocol described above, and amplified using 17 cycles of PCR. Reads were generated on a MiSeq with a 2×75 cartridge, trimmed with cutadapt, and aligned to human genome hg38. The graph of FIG. 4 shows the number of reads at each insert length, with colors representing what feature type was found at the position at which the read mapped.

That which is claimed is:

1. A method for making a cDNA library, comprising:
   (a) reverse transcribing an RNA sample that comprises mRNA to produce a first strand cDNA product;
   (b) treating the first strand cDNA product with RNAaseH to produce a digested sample that comprises fragments of the mRNA; and
   (c) reverse transcribing the mRNA fragments to produce a cDNA library.
2. The method of claim 1, further comprising sequencing the cDNA library to obtain sequence reads corresponding to at least some of the mRNA fragments.
3. The method of claim 1, wherein:
   the RNA sample of (a) further comprises small RNAs, (a) comprises reverse transcribing the mRNA but not the small RNAs to produce a first strand cDNA product that contains the small RNAs and DNA:mRNA hybrids;
   the digested sample of (b) contains the small RNAs and the mRNA fragments; and
   (c) comprises reverse transcribing the small RNAs and the mRNA fragments to produce the cDNA library, wherein the cDNA library comprises: i. copies of the small RNAs and ii. copies of the mRNA fragments.
4. The method of claim 3, wherein the small RNAs include short interfering RNA (siRNA) molecules, micro-RNA (miRNA) molecules, tiny non-coding RNA (tncRNA) molecules or small modulatory RNA (smRNA) molecules.
5. The method of claim 3, further comprising sequencing the cDNA library to obtain sequence reads corresponding to at least some of the mRNA fragments and sequence reads corresponding to at least some of the small RNAs.
6. The method of claim 1, wherein (c) is done by:
   (i) adding a tail or an adaptor to the 3' end of the RNA molecules in the digested sample;
   (ii) ligating an adaptor to the 5' end of the RNA molecules in the digested sample; and
   (iii) reverse transcribing the tailed, adaptor ligated RNAs using a primer that hybridizes to the tail or adaptor added to the 3' of the RNA molecules, to produce the cDNA library, wherein the adding (i) and the ligating (ii) can be done in either order.
7. The method of claim 1, wherein the reverse transcription of (a) is primed by an oligo-dT primer.
8. The method of claim 7, wherein (a) is done by:
   pre-heating a first mixture comprising the primer and the RNA sample to a temperature in the range of 40-80 degrees;
   pre-heating a second mixture comprising a thermo stable reverse transcriptase to a temperature in the range of 40-80 degrees; and
   admixing the first and second mixtures to produce a reaction mix; and
   incubating the reaction mix at a temperature of 40-80 degrees for at least 5 minutes, to produce the first strand cDNA product.
9. The method of claim 1, wherein the reverse transcription of (a) is primed by a sequence-specific primer.
10. The method of claim 1, wherein the method comprises amplifying the cDNA library by PCR.
11. The method of claim 10, further comprising a post-PCR size selection.
12. The method of claim 1, wherein (a) is done using an RNAaseH⁻ reverse transcriptase.
13. (The method of claim 1, wherein the reverse transcriptase activity of (a) and the RNAaseH activity of (b) are provided by a single enzyme.
14. The method of claim 1, wherein the reverse transcriptase activity of (a) and the RNAaseH activity of (b) are provided by different enzymes.
15. The method of claim 1, wherein the RNAase H is thermostable.
16. The method of claim 14, wherein the RNAase H treatment of (b) is done at temperature in the range of 60° C. to 80° C.
17. The method of claim 1, wherein the fragments produced in (b) have a median size of below 50 nucleotides.
18. The method of claim 1, wherein the RNAaseH digestion of step (b) is done using 0.1 units to 0.5 units of RNAaseH.

19. The method of claim 1, further comprising degrading or removing the first strand cDNA product before reverse transcribing the mRNA fragments to produce a cDNA library.

* * * * *